United States Patent
Hurwitz

(12) 
(10) Patent No.: US 9,549,959 B2
(45) Date of Patent: *Jan. 24, 2017

(54) ANIMAL CHEW TOY CONTAINING SOLID FOOD

(75) Inventor: Marni Markell Hurwitz, Far Hills, NJ (US)

(73) Assignee: I DID IT, Inc., Far Hills, NJ (US)

( * ) Notice: Subject to any disclaimer, the term of this patent is extended or adjusted under 35 U.S.C. 154(b) by 1033 days.

This patent is subject to a terminal disclaimer.

(21) Appl. No.: 12/229,380

(22) Filed: Aug. 22, 2008

(65) Prior Publication Data

US 2008/0314333 A1    Dec. 25, 2008

Related U.S. Application Data

(63) Continuation-in-part of application No. 11/521,900, filed on Sep. 15, 2006, now Pat. No. 8,703,174.

(51) Int. Cl.
| | | |
|---|---|---|
| *A61K 36/324* | (2006.01) | |
| *A01K 15/02* | (2006.01) | |
| *A61K 31/353* | (2006.01) | |
| *A61K 31/69* | (2006.01) | |
| *A61K 31/7008* | (2006.01) | |
| *A61K 31/7048* | (2006.01) | |
| *A61K 31/737* | (2006.01) | |
| *A61K 36/235* | (2006.01) | |
| *A61K 36/87* | (2006.01) | |
| *A61K 36/9066* | (2006.01) | |
| *A61K 38/39* | (2006.01) | |
| *A61K 45/06* | (2006.01) | |
| *A01K 11/00* | (2006.01) | |

(52) U.S. Cl.
CPC ........... *A61K 36/324* (2013.01); *A01K 15/026* (2013.01); *A23K 20/147* (2016.05); *A23K 20/174* (2016.05); *A23K 20/20* (2016.05); *A23K 50/40* (2016.05); *A61K 31/353* (2013.01); *A61K 31/69* (2013.01); *A61K 31/7008* (2013.01); *A61K 31/7048* (2013.01); *A61K 31/737* (2013.01); *A61K 36/235* (2013.01); *A61K 36/87* (2013.01); *A61K 36/9066* (2013.01); *A61K 38/39* (2013.01); *A61K 45/06* (2013.01)

(58) Field of Classification Search
CPC .... A61K 38/39; A01K 15/026; A01K 15/025; A01K 5/0114; A23K 1/1603; A23K 1/1631; A23K 1/175; A23K 1/1846
See application file for complete search history.

(56) References Cited

U.S. PATENT DOCUMENTS

| | | | |
|---|---|---|---|
| 4,802,444 A * | 2/1989 | Markham et al. | 119/710 |
| 4,804,745 A | 2/1989 | Koepff et al. | 530/356 |
| 5,162,506 A | 11/1992 | Hadden | 530/412 |
| 5,364,845 A | 11/1994 | Henderson | 514/54 |
| 5,399,347 A | 3/1995 | Trentham et al. | 424/184.1 |
| 5,419,283 A | 5/1995 | Leo | 119/709 |
| 5,587,363 A | 12/1996 | Henderson | 514/54 |
| 5,595,142 A | 1/1997 | Chill | 119/710 |
| 5,645,851 A * | 7/1997 | Moore | 424/439 |
| 5,865,146 A | 2/1999 | Markham | 119/707 |
| 5,888,514 A * | 3/1999 | Weisman | 424/94.1 |
| 6,156,355 A | 12/2000 | Shields, Jr. et al. | 426/74 |
| 6,186,096 B1 | 2/2001 | Miller | 119/709 |
| 6,237,538 B1 | 5/2001 | Tsengas | 119/707 |
| 6,238,672 B1 * | 5/2001 | Chen | 424/728 |
| 6,428,817 B1 | 8/2002 | Collin | 424/725 |
| 6,447,809 B1 * | 9/2002 | Krumhar et al. | 424/602 |
| 6,524,609 B1 | 2/2003 | Myers | 424/439 |
| 6,546,896 B1 * | 4/2003 | Markham | 119/709 |
| 6,596,303 B1 | 7/2003 | Bui et al. | 424/442 |
| 6,596,313 B2 * | 7/2003 | Rosenbloom | 424/464 |
| 6,780,841 B2 | 8/2004 | Ishaq | 514/2 |
| 6,974,841 B1 | 12/2005 | Rapisarda | 514/783 |
| 7,146,934 B1 | 12/2006 | Staley | 119/709 |
| 2003/0087008 A1 | 5/2003 | Axelrod | 426/104 |
| 2004/0137118 A1* | 7/2004 | Axelrod | 426/132 |
| 2004/0234579 A1* | 11/2004 | Finke | 424/442 |
| 2005/0100622 A1* | 5/2005 | Nair et al. | 424/777 |
| 2006/0102099 A1* | 5/2006 | Edwards | 119/710 |
| 2006/0112898 A1 | 6/2006 | Fjelstad et al. | 119/496 |
| 2006/0150919 A1* | 7/2006 | Thomason | 119/710 |
| 2008/0083378 A1 | 4/2008 | Pearce | 119/707 |

* cited by examiner

*Primary Examiner* — Mark V Stevens
(74) *Attorney, Agent, or Firm* — Ernest D. Buff, Esq.; Ernest D. Buff & Associates, LLC; Harry Anagnos

(57) ABSTRACT

An animal toy containing food having a first portion with food delivery means integrated therein adapted to securely house solid food treats, including a nutritional pet supplement, to be removed by the animal during play or through chewing action, and a second side with a plurality of gum stimulation teeth integrated within and projecting therefrom that act to massage the gums of the animal. Food delivery means may be provided as a plurality of cavities integrated within the first portion (and optionally, the second portion), preferably having a grooved or threaded interior for securely holding food pieces securely therein. Alternatively, the food delivery means is provided as a food portion composing the first portion. A pet supplement may be utilized, including joint preserving and joint rebuilding compositions comprising chicken collagen type II, glucosamine hydrochloride and chondroitin sulfate, a vitamin composition comprising vitamins C, D and K, a mineral composition comprising calcium, magnesium, zinc, copper, manganese and boron, a herbal anti-oxidant cofactor blend comprising citrus bioflavonoids, red grapes anthocyanins, turmeric rhizome, *boswellia* resin and fennel seed.

13 Claims, 9 Drawing Sheets

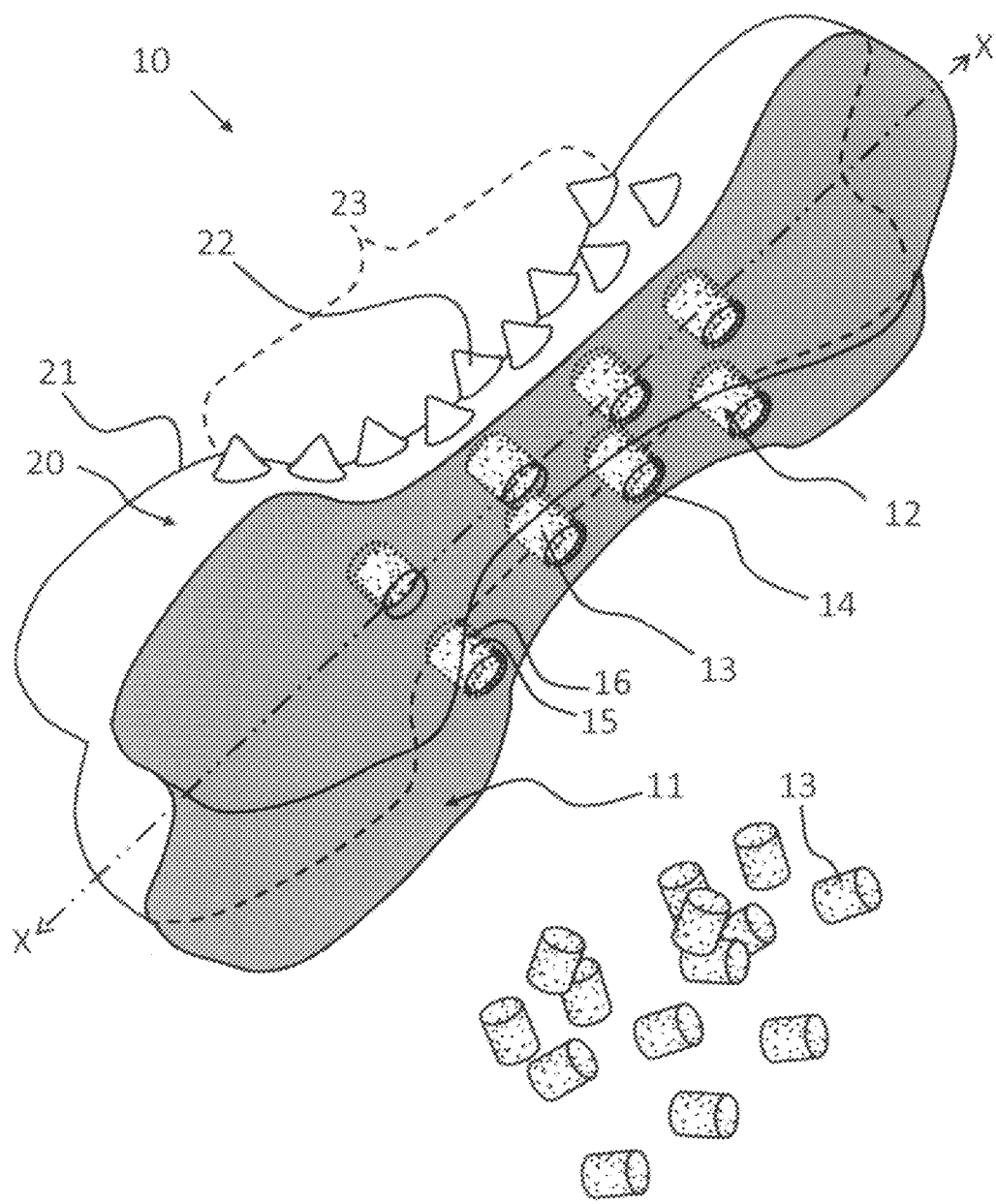

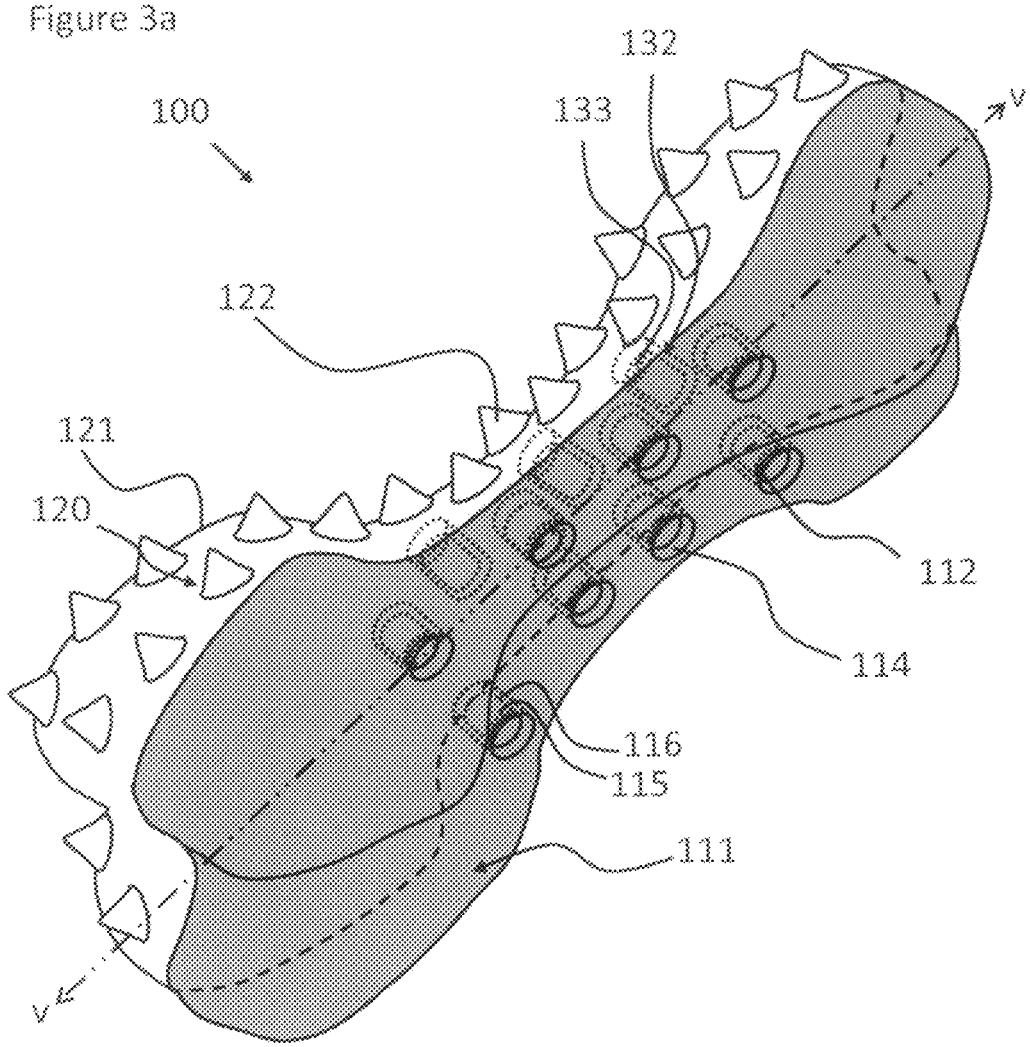

ANIMAL CHEW TOY CONTAINING SOLID FOOD

CROSS-REFERENCE TO RELATED APPLICATIONS

This application is a continuation-in-part of U.S. patent application Ser. No. 11/521,900, which was filed on Sep. 15, 2006 now U.S. Pat. No. 8,703,174, the disclosure of which is hereby incorporated in its entirety by reference thereto.

BACKGROUND OF THE INVENTION

1. Field of the Invention

The present invention relates to an animal toy containing solid food; and more particularly, to an animal toy having a first portion with food delivery means integrated therein adapted to securely house solid food treats, including a nutritional pet supplement, to be removed by the animal during play or through chewing action, and a second side with a plurality of gum stimulation teeth integrated within and projecting therefrom that act to massage the gums of the animal.

2. Description of the Prior Art

Animal/pet chew toys are known in the art. Various chew toys are composed of a sturdy material, such as a polymer, and are presented for chewing by an animal or pet. Several of these toys fail to provide delivery of a food substance, but are for chewing alone. Even where toys are provided that deliver a food substance to the animal during chewing or play, these toys are not adapted to house food separately from their construct, but rather are composed of a food material so they are eventually chewed up and consumed. For example: U.S. Pat. No. 5,419,283 to Leo discloses a chew toy composed of a starch material and a polymeric material that is edible and degradable; and U.S. Pat. App. Pub. No. 20030087008 to Axelrod discloses a molded animal chew toy with realistic appearance preferably made from ingredients that can be ingested by the animal.

Even where animal chew toys have been provided that contain or house replenish-able food or treats therein, these chew toys generally have a rubber or polymeric structure appointed with a hollow interior cavity for housing food/scented materials. For example: U.S. Pat. No. 5,595,142 to Chill discloses a therapeutic animal toy comprised of a hollow elongate body with outer surface ridges running parallel to the axis of the elongate body, inner surface circular ridges to effect a purchase of food held therein; U.S. Pat. No. 5,865,146 to Markham discloses a pet toy having an elongated hollow body extending along a longitudinal axis with first and second spaced bulbous sections; U.S. Pat. No. 6,186,096 to Miller discloses a pet chew toy having an elongated body member with a hollow cavity along its axis appointed to receive a screw rod with a hard chewable food product; U.S. Pat. No. 6,237,538 to Tsengas discloses a pet ball toy feeder which is formed from two (2) hollow semi-spherical halves; U.S. Pat. No. 7,146,934 to Staley discloses a synthetic pet chew toy and scent-training aid, formed with a hollow interior and with a plurality of small holes opening in the top and/or sides of the toy to form channels for scent dispersal to the ambient air; U.S. Pat. App. Pub. No. 20080083378 to Pearce discloses a pet toy that may be filled with food or scented material to attract and maintain the animal's interest while the pet tries to extract the material contained inside; and U.S. Pat. App. Pub. No. 20060112898 to Fjelstad et al. discloses an interactive pet toy, food delivery and training system wherein a toy object moves furtively in and out of a recess of an assembly and which when captured provides the pet an edible treat.

Further, pet and human supplements are known in the art. They comprise vitamins and minerals, various herbal products and, more recently, products that are designed to improve joint health and relieve arthritis pain. Studies have shown that collagen is a complex structural protein, which provides strength and flexibility to skin, hair and nails. Collagen is an essential and major component of muscles, tendons, cartilage, ligaments, joints and blood vessels in the human or pet body. There are three main types of collagen: I, II and III. Various agents for treatment of arthroses, and process for preparing compounds have been provided in the art, as well as pet food or nutrient formulations. See: U.S. Pat. No. 4,804,745 to Koepff et al; U.S. Pat. No. 5,162,506 to Hadden; U.S. Pat. Nos. 5,364,845 and 5,587,363 to Henderson; U.S. Pat. No. 5,399,347 to Trentham et al.; "The Effective Treatment Of Rheumatoid Arthritis (Ra) With Water-Soluble Whole Chick Collagen Type Ii Or Biologically Active Peptides Derived Therefrom", Science 261: 1727-1729, 1993; U.S. Pat. No. 6,156,355 to Shields, Jr., et al.; U.S. Pat. No. 6,428,817 to Collin; U.S. Pat. No. 6,524,609 to Myers; U.S. Pat. No. 6,596,303 to Bui et al.; U.S. Pat. No. 6,780,841 to Ishaq; and U.S. Pat. No. 6,974,841 to Rapisarda.

Notwithstanding the efforts of prior art workers to provide an animal/pet chew toy, there a is a need in the art for an animal/pet chew toy that includes gum stimulation projections or teeth integrated therein for massaging the animals gums and protecting the animals teeth from decay. Further, there is a need in the art to provide an animal pet chew toy that contains a food supplement or treat therein that is delivered to the animal during manipulation of the toy. Also, there is a need in the art for an animal pet chew toy that delivers a nutritional supplement to the animal that meets nutritional needs while at the same time protects and/or rebuilds joint tissue. Since the tissue building process requires both collagen generating compositions as well as trace minerals and vitamins at the same time, taking these vitamin supplements and joint building supplements separately does not provide this joint building and/or protecting functionality. Also there is a need for a pet toy that delivers a nutritional supplement that facilitates maintenance of the anti-oxidant level in the pet's blood stream to reduce degeneration of joint tissue by free radical associated damage.

SUMMARY OF THE INVENTION

The present invention provides an animal toy having the ability to both stimulate an animal's gums while delivering a food product to the animal. The animal chew toy includes a first portion with food delivery means adapted to securely house solid food treats, including a nutritional pet supplement, to be removed by the animal through chewing action or manipulation. On the second side of the animal chew toy are a plurality of gum stimulation teeth integrated within and projecting therefrom that act to massage the gums of the animal, helping to support a healthy mouth. The food product may include a general treat, or a nutritional pet supplement fortified with vitamins and minerals to improve or protect the health of the animal. Vitamins and minerals, as well as formula components that protect and/or build joint tissue are delivered via the pet supplement formulation, which is designed to be utilized within the animal chew toy.

The animal chew toy containing food comprises a first portion including food delivery means integrated therein. Food delivery means are adapted to deliver food to an animal during play or through chewing action and manipulation of the animal chew toy. In addition, the animal chew toy containing food comprises a second portion having an outer surface including a plurality of gum stimulation teeth integrated therein and projecting therefrom. As the animal chews on the toy, the gum stimulation teeth massage the gums increasing blood flow thereto for gum maintenance. Through manipulation of the chew toy, the food is broken into particles and the food particles are readily consumed by the animal/pet. The gum stimulation teeth integrated within the second side of the toy may cover only a segment of the outer surface of the second portion, or may cover substantially the entire outer surface of the second portion.

In one embodiment, the food delivery means comprises a plurality of cavities integrated within the first portion of the toy. These holes are each adapted to receive at least one food piece, generally having a size and shape corresponding to the holes. Preferably, each of holes include an interior wall having at least a section with grooves or presented as a threaded interior adapted to securely house each of the food pieces. Most preferably, the section of the threaded interior covers substantially the entire interior wall of each of the holes to create optimal resistance and friction in housing the food treats. Secondary food delivery means may be integrated within the second portion of the animal toy, as well as the first portion. This secondary food delivery means preferably comprises a plurality of chambers integrated within the second portion, each adapted to receive at least one food piece. Alternatively, the first portion further comprises an external surface including the plurality of gum stimulation teeth integrated therein projecting therefrom, similar to those of the second portion, to further enhance gum stimulation.

In a second embodiment, the food delivery means comprises a food portion composing the first portion, so that the first portion is edible. In this manner, the first portion is entirely consumed by the animal as the animal manipulates and chews on the toy. In this manner, the first portion of the toy is a solid food treat, and the second portion of the toy is preferably composed of rubber and having the plurality of gum stimulation teeth; thus yielding a two in one toy. Alternatively, the second portion includes secondary food delivery means comprising a plurality of chambers appointed to house food; thus yielding a two in one toy, that upon consumption of the first portion, the pet owner can load and/or reload food treats into the chambers of the second portion.

The animal chew toy can come in a plethora of shapes, sizes and colors. Preferably, the animal chew toy has a shape of a football. Most preferably, the animal chew toy has a shape of a bone. Further, the gum stimulation teeth may be of the same size or may be of varying size over the surface of the second portion (and, as in one embodiment, the first portion). Preferably, the second portion and the gum stimulation teeth are composed of a rubber material, durable in nature to with stand degradation when being chewed upon by the animal. Wherein a plurality of cavities is provided as food delivery means in the first portion of the animal chew toy, the first portion is preferably composed of a durable rubber material.

Optionally, the food may comprise a nutritious pet supplement adapted to properly balance metabolic needs that match the joint building ingredients with vitamin and trace mineral content of the formulation. The joint building ingredient chicken collagen type II is selected to have a small molecular chain with a molecular weight in the range of 5,500 to 10,000. Another joint building ingredient, glucosamine sulfate for example, needs a substantial quantity of ascorbic acid or vitamin C. However, the vitamin C of the composition is exhausted by the oxidation process of the glucosamine sulfate. More vitamin C is needed for the general upkeep of the pet. Trace copper is needed for cross-linking cartilage tissue and is provided in the mineral content in biologically usable form as chelates. The anti-oxidants provided prevent free radical damage, a key factor in preserving joints.

Generally stated, the pet supplement is provided in a single composition that is a completely mixed whereby each of the co-factors are made available to the pet's biological tissue at the same time allowing complete absorption of the nutritional formula. The formula comprises joint building components, vitamin components, mineral components, and anti-oxidant herbal components. The formulation is provided generally in the form of a biscuit or jerky treat or chewable tablet or other suitable form such as a chard, sheet or sliver adapted to dissolve on the tongue of an animal, or a powder adapted to be admixed with the animal's food; and contains a fixed quantity of these nutritional ingredients intimately mixed in a dry form. Providing proper dosage of this nutritional formulation to a pet based on its weight is extremely important. The biscuit or jerky treat is marked for a given weight size such as a 35 kilogram dog and is readily cut and proportioned according to the actual weight of the pet being treated. Likewise, the chard, sheet or sliver, as well as the powder, can be given in measured dosages depending on the animal's weight.

The formulation shown below is designed for an animal weighing 35 kilograms and has the following active ingredients.

| Joint preserving/building components | |
|---|---|
| Chicken collagen (as collagen type II) | 500-1800 mg |
| Glucosamine hydrochloride | 500-3500 mg |
| Chondroitin sulfate | 500-1500 mg |
| Vitamin components | |
| Vitamin C (as ascorbic acid) | 100-1500 mg |
| Vitamin D (as cholecalciforal) | 100-400 IU |
| Vitamin K (as phylloquinone) | 10-40 mcg |
| Mineral components | |
| Calcium (as calcium carbonate, calcium citrate, malate glycinate) | 400-600 mg |
| Magnesium (as Magnesium oxide magnesium glycinate) | 300-500 mg |
| Zinc (as zinc glycinate) | 10-20 mg |
| Copper (as copper glycinate) | 1-4 mg |
| Manganese (as manganese glycinate) | 3-8 mg |
| Boron (from Boron chelate) | 1-3 mg |
| Herbal cofactor blend | 300-1000 mg | comprising citrus bioflavonoids, red grapes anthocyanins (*vitis vinifera*) (skin), turmeric rhizome (*curcuma longa*), boswellia resin (*boswella serrata*) and fennel seed (*Foeniculum Vulgare*).

The formulation may contain inactive ingredients such as microcrystalline cellulose, croscamellose sodium, silica, magnesium stearate, pharmaceutical glaze and other ingredients that improve processability of the composition and the texture of the final product.

The preferred composition is set forth below.

| Joint preserving/building components | |
|---|---|
| Chicken collagen (as collagen type II) | 800 mg |
| Glucosamine hydrochloride | 1500 mg |
| Chondroitin sulfate | 1200 mg |

-continued

| Vitamin components | |
|---|---|
| Vitamin C (as ascorbic acid) | 100 mg |
| Vitamin D (as cholecalciforal) | 200 IU |
| Vitamin K (as phylloquinone) | 20 mcg |
| Mineral components | |
| Calcium (as calcium carbonate, calcium citrate, malate glycinate) | 500 mg |
| Magnesium (as Magnesium oxide magnesium glycinate) | 400 mg |
| Zinc (as zinc glycinate) | 15 mg |
| Copper (as copper glycinate) | 2 mg |
| Manganese (as manganese glycinate) | 5 mg |
| Boron (from Boron chelate) | 1.5 mg |
| Herbal cofactor blend | 500 mg |

Including citrus bioflavonoids, red grapes anthocyanins (*vitis vinifera*) (skin), turmeric rhizome (*curcuma longa*), boswellia resin (*boswella serrata*) and fennel seed (*Foeniculum Vulgare*).

The formulation may contain inactive ingredients such as microcrystalline cellulose, croscamellose sodium, silica, magnesium stearate, pharmaceutical glaze and other ingredients that improve processability of the composition and the texture of the final product.

The formulation has a pleasant flavor due to chicken products and is immediately consumed by pets as it is released through the food delivery means of the animal toy during manipulation by the pet. The formulation may also have additional flavor enhancers and taste enhancers for the pet.

BRIEF DESCRIPTION OF THE DRAWINGS

The invention will be more fully understood and further advantages will become apparent when reference is had to the following detailed description of the preferred embodiments of the invention and the accompanying drawings, in which:

FIG. 1a illustrates a top side view of an embodiment of the animal chew toy containing food wherein the first and second sides are preferably composed of a rubber material and the food delivery means integrated within the first side comprise a plurality of cavities housing food pieces;

FIG. 3a illustrates a top side view of an embodiment of the animal chew toy containing food wherein the first and second sides are preferably composed of a rubber material and the food delivery means integrated within the first side comprise a plurality of cavities for housing food pieces, and the second side further includes secondary food delivery means integrated therein comprising a plurality of chambers for housing food pieces;

DETAILED DESCRIPTION OF THE INVENTION

An animal toy having the ability to both stimulate an animal's gums while delivering a food product to the animal is provided by the present invention. The animal chew toy includes a first portion with food delivery means adapted to securely house solid food treats, including a nutritional pet supplement, to be removed by the animal through chewing action or manipulation. On the second side of the animal chew toy are a plurality of gum stimulation teeth integrated within and projecting therefrom that act to massage the gums of the animal, helping to support a healthy mouth. The food product may include a general treat, or a nutritional pet supplement fortified with vitamins and minerals to improve or protect the health of the animal. Vitamins and minerals, as well as formula components that protect and/or build joint tissue are delivered via the pet supplement formulation designed to be utilized within the animal chew toy.

Figure 1B:
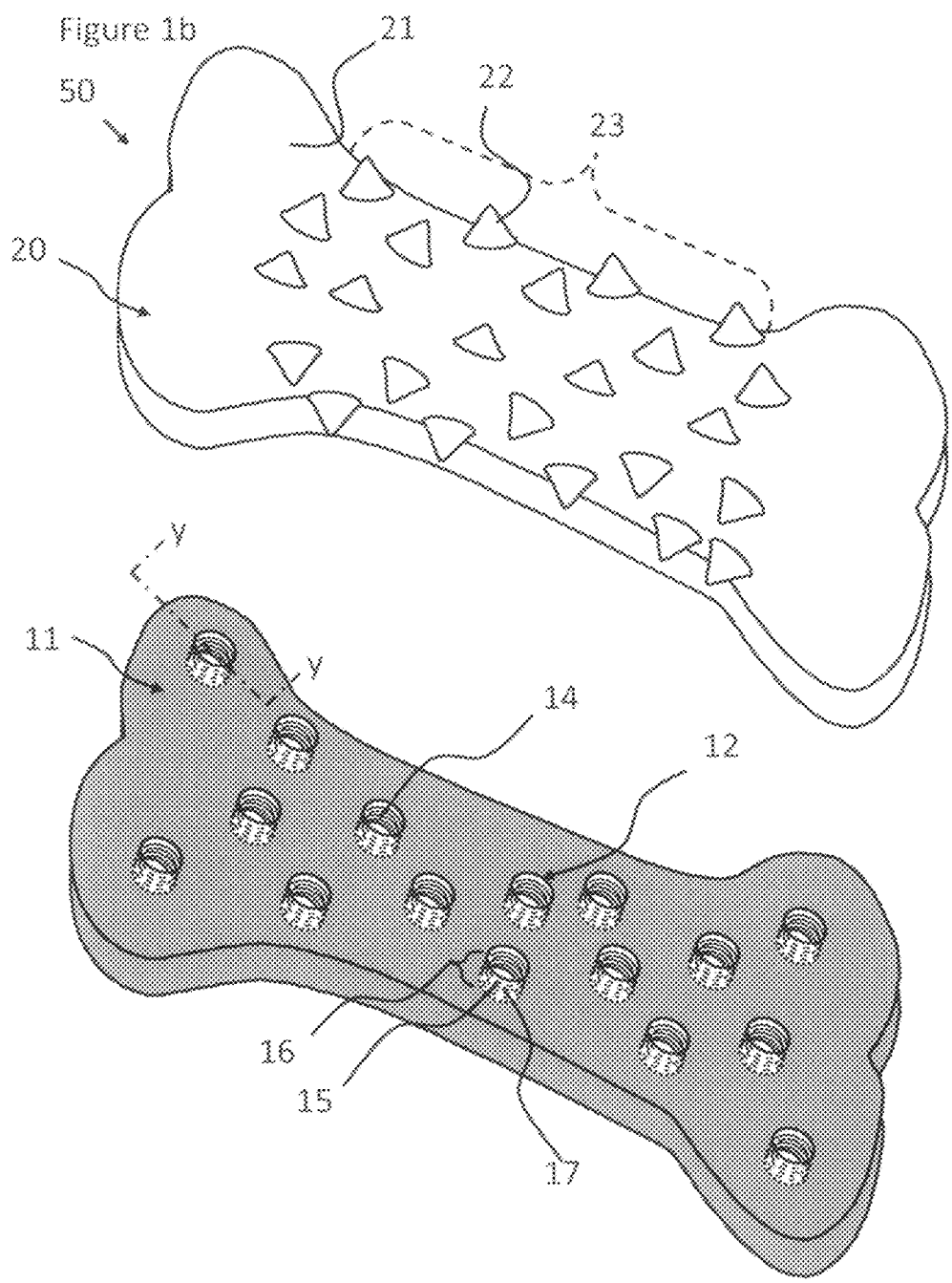
FIG. 1b illustrates a cross-sectional view taken along line x-x of FIG. 1a showing the first and second portions separated from one another.

FIGS. 1a and 1b illustrate views of an embodiment of the animal chew toy containing food wherein the first and second sides are preferably composed of a rubber material and the food delivery means integrated within the first side comprise a plurality of cavities housing food pieces. Specifically, FIG. 1a illustrates a top side view, shown generally at 10, and FIG. 1b illustrates a cross-sectional view taken along line x-x of FIG. 1a showing top views of the first and second portions separated from one another, generally shown at 50. The animal chew toy containing food 10 comprises a first portion 11 including food delivery means 12 integrated therein. Food delivery means 12 are adapted to deliver food 13 to an animal during play or through chewing action and manipulation of animal chew toy 10. Such food products may include tasty or savory treats, supplements, vitamins, medications, breathe products, etc. In addition, animal chew toy containing food 10 comprises a second portion 20 having an outer surface 21 including a plurality of gum stimulation teeth 22 integrated therein and projecting therefrom. Gum stimulation teeth 22 integrated within second side 20 of toy 10 may cover only a segment 23 of outer surface 21, as shown, or may substantially cover the entire outer surface 21 of second portion 20.

In the embodiment shown in FIGS. 1a-1b, food delivery means 12 comprises a plurality of cavities 14 integrated within first portion 11 of toy 10. These cavities 14 are each adapted to receive at least one food piece 13, generally having a size and shape corresponding to cavities 14. Preferably, each cavity 14 includes an interior wall 15 having at least a section 16 with grooves or presented as a threaded interior 17 adapted to securely house each of food piece 13. Most preferably, section 16 of threaded interior 17 substantially covers interior wall 15 of each cavity 14 to create optimal resistance and friction in housing food treats 13 (see FIGS. 2a-2c for illustrations). As the animal chews on toy 10, gum stimulation teeth 22 massage the gums increasing blood flow thereto for healthy gum maintenance. Through manipulation of chew toy 10, food 13 is broken into particles and food particles are readily consumed by the animal/pet. Herein, chew toy 10 is shown in the shape of a bone, however, chew toy 10 may have a plethora of shapes and come in various sizes and colors (for examples, see FIG. 4). Gum stimulation teeth 22 may be of the same size or may be of varying size over outer surface 21 of second portion 20. Preferably, second portion 20 and the gum stimulation teeth 22 are composed of a rubber material, durable in nature to with stand degradation when being chewed upon by the animal. Wherein a plurality of cavities 14 is provided as food delivery means 12 in first portion 11, first portion 11 is preferably composed of a durable rubber material.

Figure 2A:
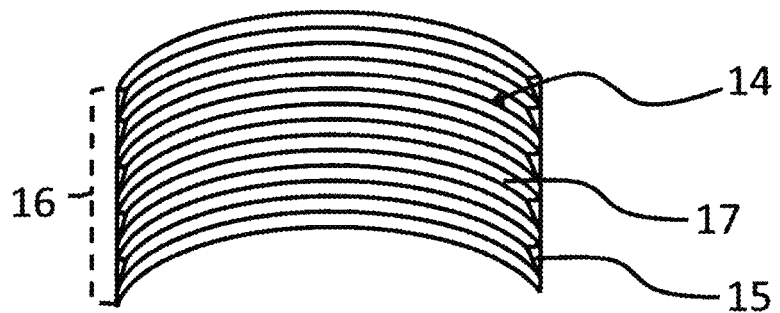
FIG. 2a illustrates a cross-sectional view taken along y-y of FIG. 1b, showing an embodiment of the plurality of cavities wherein the section of the threaded interior substantially covers the interior wall of each of the holes.
Figure 2B:
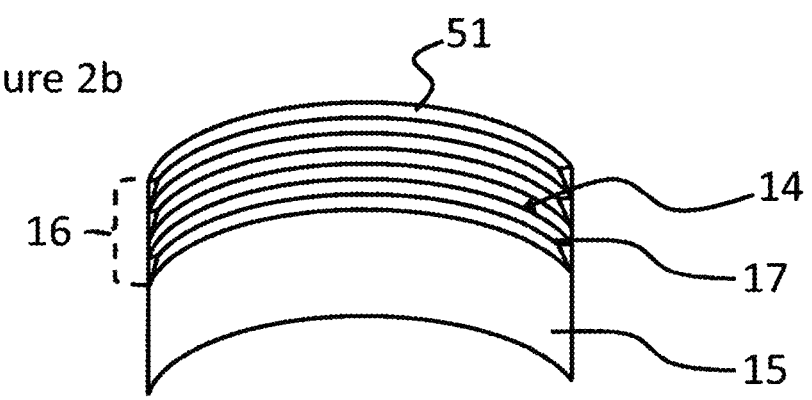
FIG. 2b illustrates a cross-sectional view taken along y-y of FIG. 1b, showing an embodiment of the plurality of cavities wherein the section of the threaded interior is shown near just the top aperture of each of the holes.
Figure 2C:
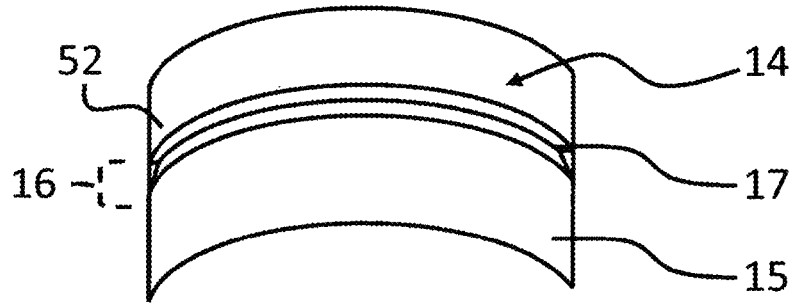
FIG. 2c illustrates a cross-sectional view taken along y-y of FIG. 1b, showing an embodiment of the plurality of cavities wherein the section of the threaded interior is shown substantially in the center of each of the holes.

FIGS. 2a-2c illustrate cross-sectional views of cavities 14 of FIGS. 1a-1b taken along y-y of FIG. 1b. FIG. 2a illustrates a cross-sectional view taken along y-y of FIG. 1b, showing an embodiment of the plurality of cavities 14 wherein section 16 of threaded interior 17 substantially covers interior wall 15 of each cavity 14. FIG. 2b illustrates a cross-sectional view taken along y-y of FIG. 1b, showing an embodiment of the plurality of cavities 14 wherein section 16 of threaded interior 17 is shown near just the top aperture 51 of each of the cavities 14. FIG. 2c illustrates a cross-sectional view taken along y-y of FIG. 1b, showing an embodiment of the plurality of cavities 14 wherein section 16 of threaded interior 17 is shown substantially in a center 52 of each of the cavities 14. These threads or groove are of a screw like design causing the pet to work harder to achieve its goal, which is getting the food/supplement/breathe product/etc. out of the holes/cavities. The grooves or threads are molded in the interior of each cavity to make it more challenging for the dog when trying to get at the treat placed inside the holes/cavity. The threads/grooves securely holds the food in place by increasing resistance against the release of the food supplement for an extended period of time.

Figure 3B:
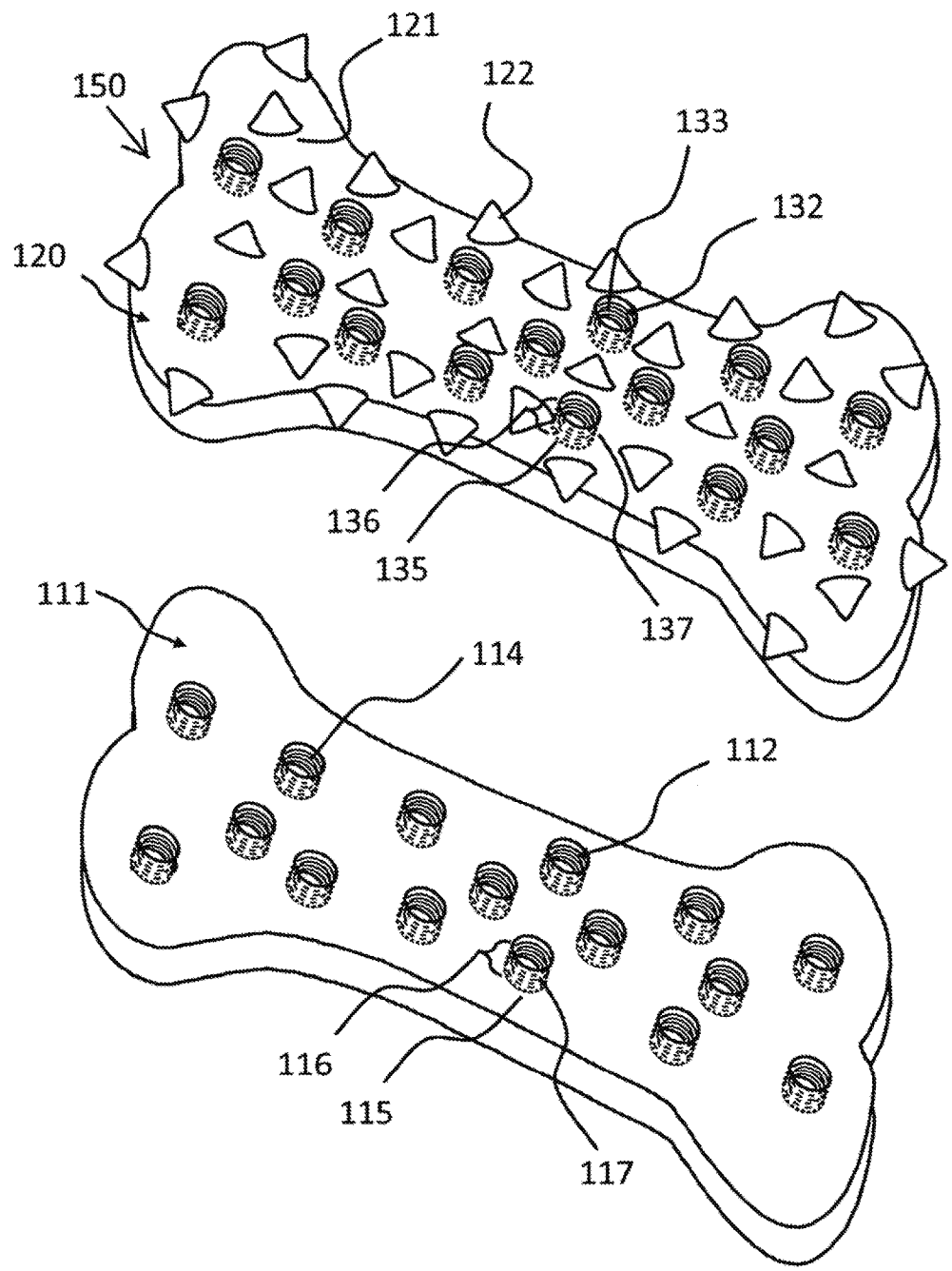
FIG. 3b illustrates a cross-sectional view taken along line v-v of FIG. 3a showing the first and second portions separated from one another.

FIGS. 3a and 3b illustrate views of an embodiment of the animal chew toy containing food wherein the first and second sides are preferably composed of a rubber material and the food delivery means integrated within the first side comprise a plurality of cavities for housing food pieces, and the second side further includes secondary food delivery means integrated therein comprising a plurality of chambers for housing food pieces. Specifically, FIG. 3a illustrates a top side view, shown generally at 100, and FIG. 3b illustrates a cross-sectional view taken along line v-v of FIG. 3a showing top views of the first and second portions separated from one another, generally shown at 150. The animal chew toy containing food 100 comprises a first portion 111 including food delivery means 112 integrated therein adapted to deliver food to an animal. A second portion 120 is provided having an outer surface 121 including a plurality of gum stimulation teeth 122 integrated therein and projecting therefrom. Gum stimulation teeth 122 integrated within second side 120 may cover only a segment of outer surface 121, or may substantially cover the entire outer surface 121 of second portion 120 as shown. In this embodiment, food delivery means 112 comprises a plurality of cavities 114 integrated within first portion 111. These cavities 114 are each adapted to receive at least one food piece. Preferably, each cavity 114 includes an interior wall 115 having at least a section 116 with grooves or presented as a threaded interior 117 adapted to securely house each food piece. Preferably, second portion 120 includes secondary food delivery means 132 comprising a plurality of chambers 133 each adapted to receive at least one food piece, that work in conjunction with food delivery means 112 of first portion 111 to deliver food particles to the animal, while gum stimulation teeth 122 act to massage the gums. Chambers 133 of secondary food delivery means 132 of second portion 120 preferably includes a core wall 135 having at least a sector 136 with grooves or presented as a threaded or grooved interior 137 adapted to securely house each food piece (best seen and illustrated in FIG. 3b).

Figure 4:
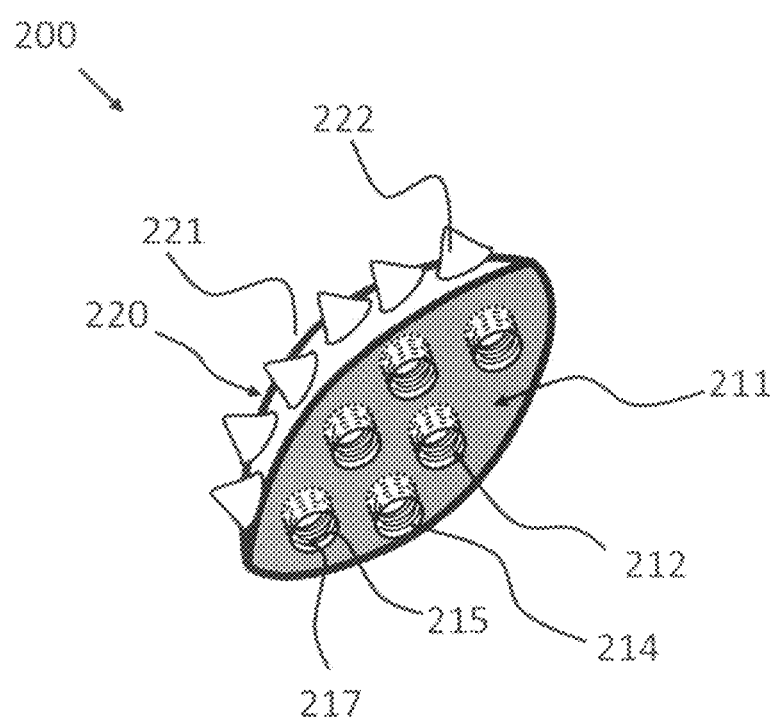
FIG. 4 illustrates a top side view of an embodiment of the animal chew toy containing food shaped as a football wherein the first and second sides are preferably composed of a rubber material and the food delivery means integrated within the first side comprise a plurality of cavities for housing food pieces.

The animal chew toy containing food can be constructed having a plethora of shapes, in a plethora of sizes and colors. FIG. 4 illustrates a top side view of an embodiment of the animal chew toy containing food shaped as a football, shown generally at 200. The animal chew toy containing food 200 comprises a first portion 211 including food delivery means 212 integrated therein. A second portion 220 is provided having an outer surface 221 including a plurality of gum stimulation teeth 222. In this embodiment, food delivery means 212 comprises a plurality of cavities 214 adapted to receive at least one food piece. Preferably, each cavity 214 includes an interior wall 215 having at least a section with grooves or presented as a threaded interior 217 adapted to securely house each food piece.

Figure 5:
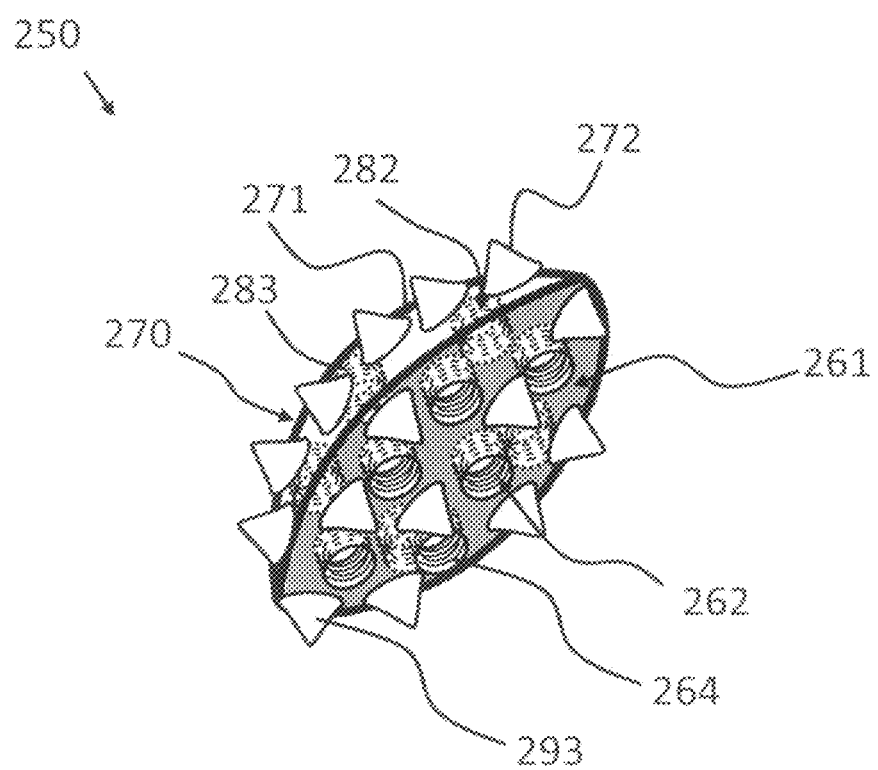
FIG. 5 illustrates a top side view of an embodiment of the animal chew toy containing food shaped as a football wherein the first and second sides are preferably composed of a rubber material and food delivery means are integrated in both the first and second sides, comprising a plurality of cavities and chambers, respectively, for housing food pieces, and the first side further includes a plurality of gum stimulation teeth.

FIG. 5 illustrates a top side view of an embodiment of the animal chew toy containing food shaped as a football, shown generally at 250, comprising a first portion 261 including food delivery means 262 integrated therein. A second portion 270 is provided having an outer surface 271 including a plurality of gum stimulation teeth 272. In this embodiment, food delivery means 262 comprises a plurality of cavities 264 adapted to receive at least one food piece. Further, second side 270 includes secondary food delivery means 282 comprising a plurality of chambers 283 each adapted to receive at least one food piece. Preferably, each cavity 214 and chamber 283 includes a grooved or threaded interior wall securely housing each food piece. Additionally, first side 261 further comprises an external surface 291 including the plurality of gum stimulation teeth 293 integrated therein projecting therefrom.

Figure 6:
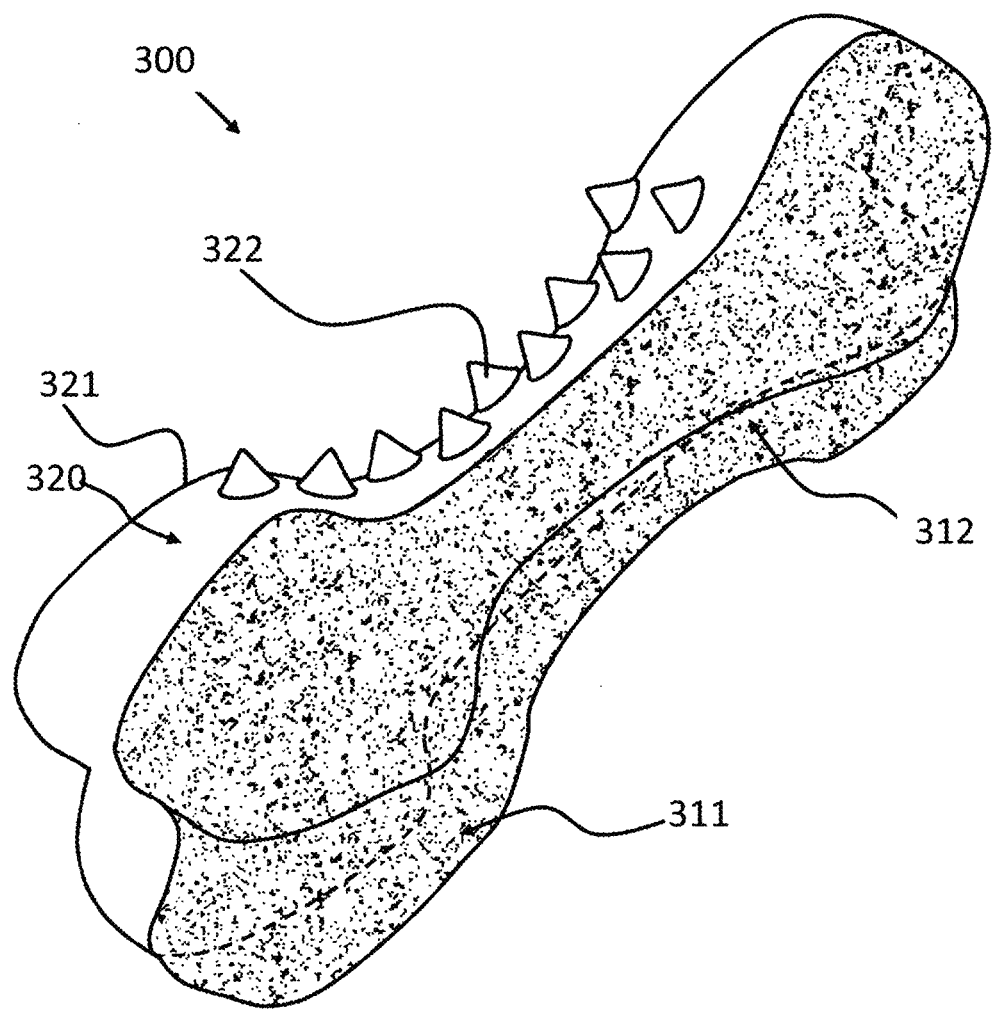
FIG. 6 illustrates a top side view of an embodiment of the animal chew toy containing food wherein the second side is preferably composed of a rubber material and the food delivery means comprises a food portion composing the first portion, so that the first portion is substantially edible.

In another embodiment, the food delivery means comprises a food portion composing the first portion, so that the first portion is edible. In this manner, the first portion is entirely consumed by the animal as the animal manipulates and chews on the toy. FIG. 6 illustrates a top side view of an embodiment of the animal chew toy containing food wherein the second side is preferably composed of a rubber material and the food delivery means comprises a food portion composing the first portion, so that the first portion is substantially edible, shown generally at 300. The animal chew toy containing food 300 comprises a first portion 311 including food delivery means 312 integrated therein adapted to deliver food to an animal. In this embodiment, food delivery means 312 comprises a food portion composing first portion 311, so that first portion 311 is edible. A second portion 320 is provided having an outer surface 321 including a plurality of gum stimulation teeth 322 integrated therein and projecting therefrom. Gum stimulation teeth 322 integrated within second side 320 may cover only a segment of outer surface 321 (as shown), or may substantially cover the entire outer surface 321 of second portion 320. After first portion 311 is consumed, second portion 320 can remain as a chew toy, but not longer contains food portions. In this manner, the first portion of the toy is a solid food treat, and the second portion of the toy is preferably composed of rubber and having the plurality of gum stimulation teeth; thus yielding a two in one toy.

Figure 7:
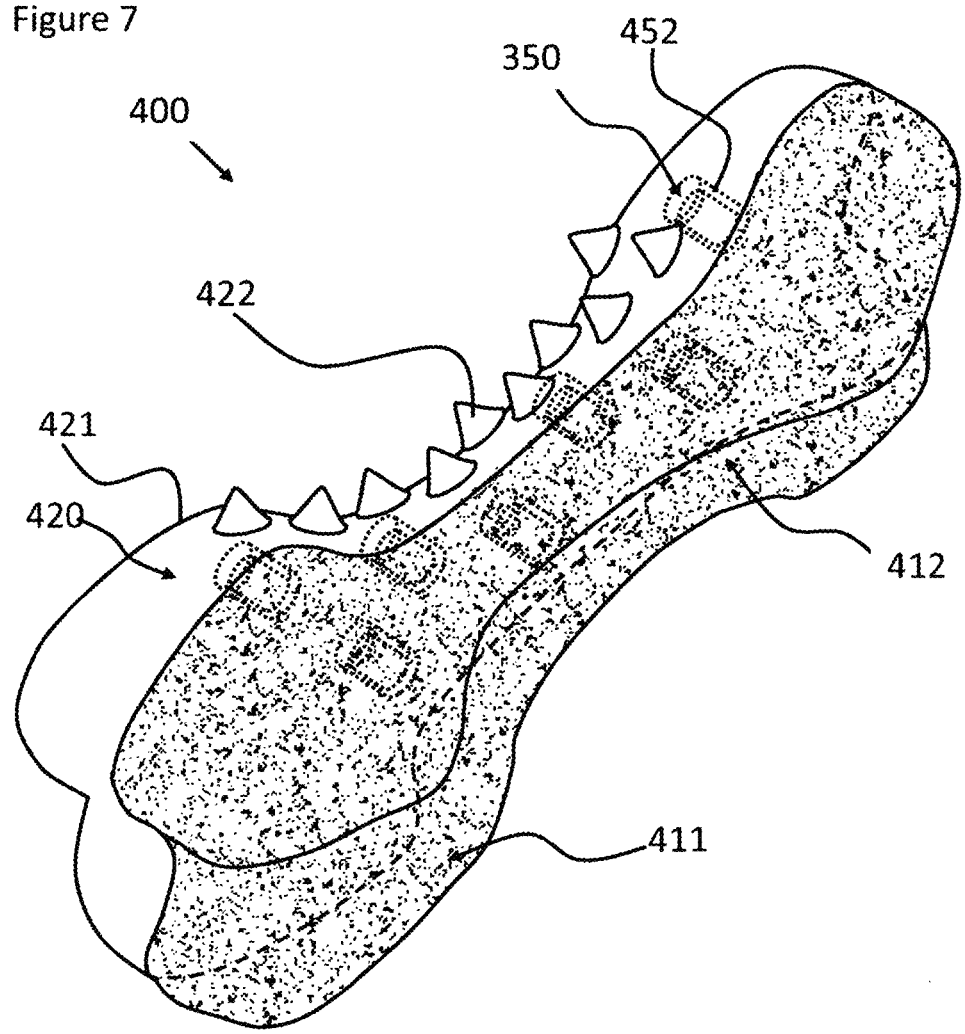
FIG. 7 illustrates a top side view of an embodiment of the animal chew toy containing food wherein the second side is preferably composed of a rubber material and includes a secondary food delivery means comprising a plurality of chambers, while the food delivery means comprises a food portion composing the first portion, so that the first portion is substantially edible and the second portion can be utilized to continue to provide food treats by simply refilling the chambers therein.

FIG. 7 illustrates a top side view of an embodiment of the animal chew toy containing food wherein the second side is preferably composed of a rubber material and includes a secondary food delivery means comprising a plurality of chambers, while the food delivery means comprises a food portion composing the first portion, so that the first portion is substantially edible and the second portion can be utilized to continue to provide food treats by simply refilling the chambers therein, shown generally at 400. The animal chew toy containing food 400 comprises a first portion 411 including food delivery means 412 comprising a food portion composing first portion 411, so that first portion 411 is edible. A second portion 420 is provided having an outer surface 421 including a plurality of gum stimulation teeth 422. Second portion 420 further comprises a secondary food delivery means 450 comprising a plurality of chambers 452 for housing food pieces. In this arrangement, after first portion 411 is consumed, second portion 420 can remain as a chew toy which can be utilized to continue to provide food treats by simply refilling chambers 452 therein. In this manner, the first portion of the toy is a solid food treat, and the second portion of the toy is preferably composed of rubber and having the plurality of gum stimulation teeth and including secondary food delivery means comprising a plurality of chambers appointed to house food; thus yielding a two in one toy, that upon consumption of the first portion, the pet owner can load and/reload food treats into the chambers of the second portion.

Optionally, the food may comprise a nutritious pet supplement adapted to properly balance metabolic needs that match the joint building ingredients with vitamin and trace mineral content of the formulation. Antioxidants are provided in the form of a herbal co-factor blend in the formulation. The antioxidants reduce the activity of free radicals which, when present, contribute to joint degradation. The formulation is supplied as a ready to use paste, biscuit, jerky treat, chewable tablet; or a chard or sheet adapted to dissolve on the tongue of an animal; or a powder adapted to be admixed with the animal's food; which carries a fixed quantity of these joint preserving/joint rebuilding components, vitamin components, mineral components and an anti-oxidant, herbal co-factor blend for a fixed weight pet. Product containing the formulation is thereafter cut into segments, or administered in measured dosages, that are size and weight proportioned in accordance with the weight of the animal being treated.

Collagen occurs in many places throughout the body, and occurs in different forms known as types, which include: Type I collagen—This is the most abundant collagen of the body. It is present in scar tissue, the end product when tissue heals by repair. It is found in tendons and the organic part of bone. Type II collagen—Articular cartilage. Type III collagen—This is the collagen of granulation tissue, and is produced quickly by young fibroblasts before the tougher type I collagen is synthesized. Type IV collagen—basal lamina; eye lens Type V collagen—most interstitial tissue, assoc. with type I, associated with placenta Type VI collagen—most interstitial tissue, associated with type I. Type VII collagen—forms anchoring fibrils in dermal epidermal junctions. Type VIII collagen—some endothelial cells. Type IX collagen—FACIT collagen, cartilage, assoc. with type II and XI fibrils. Type X collagen—hypertrophic and mineralizing cartilage. Type XI collagen—cartilage. Type XII collagen—FACIT collagen, interacts with type I containing fibrils, decorin and glucosaminoglycans. Type XIII collagen—transmembrane collagen, interacts with integrin albl, fibronectin and components of basment membranes like nidogen and perlecan. As many as 28 types of collagen have previously been described in the literature.

One of the key elements of the composition of the nutritional food product adapted to be utilized in the animal chew toy of the present invention is the inclusion of chicken collagen type II. Chicken collagen type II is extracted from the sternum (breast) bones of young chickens, which contain a large fraction of type II collagen. Type II collagen is the key type of collagen present in the joints. In addition, this extracted type II collagen also contains trace amounts of copper, which facilitates cross linking of collagen polymer chains to create high strength joints. As recently discussed by David E. Trentham, Roselynn A. Dynesius-Trentham, E. John Orav, Daniel Combitchi, Carlos Lorenzo, Kathryn Lea Sewell, David A. Hafler, and Howard L. Weiner in a paper entitled "Effects of Oral Administration of Type II Collagen on Rheumatoid Arthritis" published in journal of Science 261:1727-1729, 1993, it is clear that this chicken collagen of type II can be ingested orally and travel through the gastrointestinal tract without degradation. The mechanism of action exhibited by type II chicken collagen is believed to occur via oral tolerization to autoantigens. In addition, the digested type II chicken collagen also contains approximately 20% of depolymerized chondroitin sulfate and 10% of hyaluronic acid (HA) as indicated in U.S. Pat. No. 6,780,841. HA acts as a lubricant between connective tissues of the skin and protects the joints by providing shock-absorption. Decrease in HA levels is commonly associated with a great variety of disorders and ailments. For example, osteoarthritis patients experience decreased levels of HA in their synovial fluid. This has a detrimental effect on the joints because HA is primarily responsible for the lubricating and shock-absorbing effects of the synovial fluid. For this reason, researchers have theorized that the replacement of such lost HA may help osteoarthritis sufferers to rebuild damaged cartilage and to regain joint movement. Therefore, the key element of the invention is to add type II chicken collagen that can be orally ingested in combination with a well-balanced vitamin and mineral formulation with added antioxidants.

The length of the polymeric chain of the chicken collagen type II has a lot to do with its absorption in the animal's gastrointestinal tract. Smaller length chains are more easily absorbed. A digested chicken collagen type II with a molecular weight of 5.500 to 10,000 is ideally suited for the formulation since it absorbs at nearly the same rate as the vitamin, mineral and herbal co-factor blend of the supplement formulation.

Glucosamine is an amino sugar made of molecules called Glucosaminolglycans or "GAGS". GAGS are found in almost every tissue of the body including joints, tendons, ligaments, cartilage, skin and blood vessels. Glucosamine is needed to maintain normal joint fluid. Joint fluid surrounds the joints providing them with important nutrients. It helps to lubricate and cushion the joints, acting like a shock absorber during movement and insulating the bones from friction. Glucosamine is necessary to maintain the overall health and integrity of cartilage, bones and joints. It may also enhance the dog's mobility and flexibility.

Vitamin C is needed to regenerate and revitalize Vitamin E. It is also essential to normal collagen formation. Collagen is an integral part of the walls of the blood vessels and is part of the matrix of cartilage, tendons, ligaments, bones and skin.

Vitamin D plays an important role in the maintenance of an intact and strong skeleton. Its primary task is to regulate the amount of calcium and phosphorus in the blood by ensuring correct intake from intestines and secretion. Vitamin D3: cholecalciferol (made from 7-dehydroccavitiesterol), calcidiol, and calcitriol Calcium is essential for the normal growth and maintenance of bones and teeth. Calcium requirements must be met throughout the life of a pet. Long-term calcium deficiency can lead to osteoporosis, in which the bone deteriorates and there is an increased risk of fractures.

Magnesium ion is essential to the basic nucleic acid chemistry of life, and thus is essential to all cells of all known living organisms. Many enzymes require the presence of magnesium ions for their catalytic action, especially enzymes utilizing ATP, or those which use other nucleotides to synthesize DNA and RNA.

Zinc is an essential mineral and is a vital component of several biochemical and enzymatic reactions in a dog's body. In addition, zinc is needed to maintain the health and integrity of a dog's skin and hair coat.

Copper is essential in animals. Copper is carried mostly in the bloodstream on a plasma protein called ceruloplasmin. When copper is first absorbed in the gut it is transported to the liver bound to albumin. Copper is found in a variety of enzymes, including the copper centers of cytochrome c oxidase and the enzyme superoxide dismutase (containing copper and zinc). In addition to its enzymatic roles, copper is used for biological electron transport. The blue copper proteins that participate in electron transport include azurin and plastocyanin. The name "blue copper" comes from their intense blue color arising from a ligand-to-metal charge transfer (LMCT) absorption band around 600 nm. Copper is also essential in cross linking collagen.

Manganese is a trace mineral needed for vital enzyme reactions and proper bone development. It plays a key role in supporting the bodied production of vital elements required to rebuild cartilage in damaged joints.

Boron can drop excretion of calcium by 44%, and activate estrogen and vitamin D. This prevents bone loss.

Citrus bioflavonoids have been referred to as "nature's biological response modifiers" because of strong experimental evidence of their ability to modify the body's reaction to allergens, viruses, and carcinogens. They show anti-allergic, anti-inflammatory, anti-microbial and anti-cancer activity. In addition, flavonoids act as powerful antioxidants, protecting against oxidative and free radical damage.

Red grape anthocyanins are present together with other natural pigments like the closely chemically related flavonoids, carotenoids, anthoxanthins and betacyanins with similar anti-oxidant functionality.

Turmeric contains Curcumin has been used for thousands of years as a safe anti-inflammatory in a variety of ailments as part of Indian traditional medicine.

*Boswellia* is a genus of trees known for their fragrant resin, which has many pharmacological uses particularly as anti-inflammatories.

The preferred formulation is designed for an animal weighing 35 kilograms and has the following ingredients.

| Joint preserving/building components | |
| --- | --- |
| Chicken collagen (as collagen type II) | 800 mg |
| Glucosamine hydrochloride | 1500 mg |
| Chondroitin sulfate | 1200 mg |
| Vitamin components | |
| Vitamin C (as ascorbic acid) | 100 mg |
| Vitamin D (as cholecalciforal) | 200 IU |
| Vitamin K (as phylloquinone) | 20 mcg |
| Mineral components | |
| Calcium (as calcium carbonate, calcium citrate, malate glycinate) | 500 mg |
| Magnesium (as Magnesium oxide magnesium glycinate) | 400 mg |
| Zinc (as zinc glycinate) | 15 mg |
| Copper (as copper glycinate) | 2 mg |
| Manganese (as manganese glycinate) | 5 mg |
| Boron (from Boron chelate) | 1.5 mg |
| Herbal cofactor blend | 500 mg |

Including citrus bioflavonoids, red grapes anthocyanins (*vitis vinifera*) (skin), turmeric rhizome (*curcuma longa*), boswellia resin (*boswella serrata*) and fennel seed (*Foeniculum Vulgare*).

The formulation may contain inactive ingredients such as microcrystalline cellulose, croscamellose sodium, silica, magnesium stearate, pharmaceutical glaze and other ingredients that improve processability of the composition and the texture of the final product.

The formulation has a pleasant flavor due to chicken products and is immediately consumed by pets. The formulation may also have additional flavor enhancers and taste enhancers for the pet.

The key features of the joint preserving nutritional vitamin, mineral and herbal pet supplement include, in combination, the components set forth below:

1. a group of joint preserving/joint rebuilding compositions comprising chicken collagen type II, glucosamine hydrochloride and chondroitin sulfate incorporated within the pet supplement;
2. a group of vitamins comprising vitamin C, vitamin D and vitamin K incorporated within the pet supplement;
3. a group of minerals comprising calcium as calcium carbonate, calcium citrate, calcium malate or calcium glycinate, magnesium magnesium oxide or magnesium glycinate, zinc glycinate, copper glycinate, manganese glycinate and boron chelate incorporated within the pet supplement;
4. an anti-oxidant herb blend comprising citrus bioflavonoids, red grapes anthocyanins (*vitis vinifera*), turmeric rhizome (*curcuma longa*), boswellia resin (*boswella serrata*) and fennel seed (*Foeniculum Vulgare*) incorporated within the pet supplement;
5. the pet supplement having a dry mixed joint preserving/joint rebuilding composition, vitamin composition, mineral composition and herbal co-factor blend with a recipe designed for a certain weight of a pet and the supplement proportioned according to the weight of the pet being treated by the user;

6. the joint preservation/joint rebuilding process being optimized by synergic interaction of each of the compositions of the pet supplement delivered orally through the gastrointestinal tract of the animal simultaneously;

7. the pet supplement, delivered as a past, biscuit, jerky treat or chewable tablet; or as a sheet, chard or sliver adapted to dissolve on the tongue of an animal; or a powder appointed to be admixed with the animal's food, with pleasant chicken flavor, provides joint health and nutritional benefits to the pet through a single dose.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. An animal chew toy containing food, comprising:
   a. a first portion including food delivery means integrated therein adapted to deliver said food to an animal during play or through chewing action and manipulation of said animal chew toy, said first portion further comprising an external surface including a plurality of gum stimulation teeth being of varying size integrated therein and projecting therefrom;
   b. a second portion being structurally connected to said first portion, said second portion having an outer surface including a plurality of gum stimulation teeth being of varying size integrated therein and projecting therefrom;
   c. said food delivery means comprising a plurality of cavities integrated within said first portion, each adapted to receive at least one food piece;
   d. each of said plurality of cavities including an interior wall, at least a section of said interior wall being a threaded interior adapted to securely house each of said food pieces, said section of said threaded interior substantially covering said interior wall;
   e. said gum stimulation teeth substantially cover said outer surface of said second portion;
   f. said second portion further comprises secondary food delivery means;
   g. said secondary food delivery means comprises a plurality of chambers integrated within said second portion each adapted to receive at least one food piece;
   h. said food is a pet supplement, comprising:
      i. a joint preserving/joint rebuilding composition comprising type II chicken collagen in a range of 500 mg to 1800 mg, glucosamine hydrochloride in a range from 500 mg to 3500 mg and chondroitin sulfate in a range from 500 mg to 1500 mg;
      ii. a vitamin composition that works in conjunction with said joint preserving/joint rebuilding composition comprising Vitamin C, Vitamin D and Vitamin K;
      iii. a mineral composition comprising calcium as calcium carbonate, calcium citrate, calcium malate or calcium glycinate, magnesium as magnesium oxide or magnesium glycinate, zinc glycinate, copper glycinate, manganese glycinate and boron chelate; and
      iv. a herbal cofactor blend in a range from 300 mg to 1000 mg comprising citrus bioflavonoids, red grapes anthocyanins, turmeric rhizome, *boswellia* resin and fennel seed;
   i. said food delivery means being edible; and
   j. said second portion and said gum stimulation teeth being composed of a rubber material;
   whereby said joint preserving/joint rebuilding composition, vitamin composition, mineral composition, and herbal cofactor blend are mixed in the supplement and orally delivered to the pet as segments proportioned according to pet weight, thereby providing vitamin and mineral nutrition and synergistic action especially suited to rebuild the pet's joints and preserve the pet's joint health.

2. An animal chew toy as recited by claim 1, wherein said animal chew toy has a shape of a football.

3. An animal chew toy as recited by claim 1, wherein said animal chew toy has a shape of a bone.

4. An animal chew toy as recited by claim 1, wherein said type II chicken collagen has a molecular weight of 5,500 to about 10,000.

5. An animal chew toy as recited by claim 1, wherein said vitamin C is present in an amount ranging from 100 mg to 1500 mg for a pet weighing 35 kilograms.

6. An animal chew toy as recited by claim 1, wherein said vitamin D is present in an amount ranging from 100 IU to 400 IU for a pet weighing 35 kilograms.

7. An animal chew toy as recited by claim 1, wherein said vitamin K is present in an amount ranging from 10 mcg to 40 mcg for a pet weighing 35 kilograms.

8. An animal chew toy as recited by claim 1, wherein said calcium is present in an amount ranging from 400 mg to 600 mg for a pet weighing 35 kilograms.

9. An animal chew toy as recited by claim 1, wherein said magnesium is present in an amount ranging from 300 mg to 500 mg for a pet weighing 35 kilograms.

10. An animal chew toy as recited by claim 1, wherein said zinc is present in an amount ranging from 10 mg to 20 mg for a pet weighing 35 kilograms.

11. An animal chew toy as recited by claim 1, wherein said copper is present in an amount ranging from 1 mg to 4 mg for a pet weighing 35 kilograms.

12. An animal chew toy as recited by claim 1, wherein said manganese is present in an amount ranging from 3 mg to 8 mg for a pet weighing 35 kilograms.

13. An animal chew toy as recited by claim 1, wherein said boron is present in an amount ranging from 1 mg to 3 mg for a pet weighing 35 kilograms.

* * * * *